US008359207B2

(12) United States Patent  
Backer et al.

(10) Patent No.: US 8,359,207 B2
(45) Date of Patent: Jan. 22, 2013

(54) METHOD AND APPARATUS FOR GENERATING TOXICOLOGY REPORTS

(75) Inventors: Ronald C. Backer, Midland, TX (US);
William Pace, Baytown, TX (US);
Patricia Patrick, Decatur, GA (US);
Sybil Patricia Lowry, Houston, TX (US); Shesh Rau, Naperville, IL (US);
Joel McEndree, Midland, TX (US)

(73) Assignee: Ameritox, Ltd., Midway, TX (US)

( * ) Notice: Subject to any disclaimer, the term of this patent is extended or adjusted under 35 U.S.C. 154(b) by 499 days.

(21) Appl. No.: 11/949,407

(22) Filed: Dec. 3, 2007

(65) Prior Publication Data

US 2008/0183503 A1    Jul. 31, 2008

Related U.S. Application Data

(60) Provisional application No. 60/868,225, filed on Dec. 1, 2006.

(51) Int. Cl.
*A61B 5/00* (2006.01)

(52) U.S. Cl. .......... 705/3; 705/14.56; 702/118; 702/19; 436/56; 436/518

(58) Field of Classification Search ........... 705/3, 14.56; 702/118, 19; 436/56, 518
See application file for complete search history.

(56) References Cited

U.S. PATENT DOCUMENTS

| | | | |
|---|---|---|---|
| 6,801,916 B2 * | 10/2004 | Roberge et al. | 1/1 |
| 6,873,914 B2 * | 3/2005 | Winfield et al. | 702/19 |
| 7,158,890 B2 * | 1/2007 | Brumbach et al. | 702/19 |
| 2002/0081750 A1 * | 6/2002 | Ernest et al. | 436/518 |
| 2004/0006499 A1 * | 1/2004 | Vergopoulos et al. | 705/7 |
| 2004/0073464 A1 | 4/2004 | Huang | |
| 2005/0233459 A1 | 10/2005 | Melker et al. | |
| 2006/0019400 A1 * | 1/2006 | LaCourse et al. | 436/93 |
| 2006/0047538 A1 | 3/2006 | Condurso et al. | |
| 2006/0265173 A1 | 11/2006 | Mishima et al. | |
| 2007/0214010 A1 * | 9/2007 | Beaver et al. | 705/2 |

OTHER PUBLICATIONS

ProQuest search result, Sep. 12, 2012.*
Written Opinion of the International Searching Authority for International Application No. PCT/US2008/085403, dated Feb. 10, 2009.
International Search Report for International Application No. PCT/US 07/086271 of Applicants Backer, et al.
Official Report for Australian Patent Application No. 2007329499 mailed May 2, 2012.

* cited by examiner

*Primary Examiner* — Dilek B Cobanoglu
(74) *Attorney, Agent, or Firm* — K&L Gates LLP (57) ABSTRACT

The present disclosure provides methods and apparatuses for generating toxicology reports. Using the methods and apparatus disclosed herein, physicians can more easily understand toxicological lab test results. Physicians receive a toxicology report that explains, in plain language, the toxicological lab test results. A rules engine provides rules for interpreting the toxicological lab test results. Detailed explanations are associated with the rules, and the explanations appear on the toxicology report. The toxicology report greatly reduces the need for the physician to call the toxicology scientist.

30 Claims, 6 Drawing Sheets

Patient Name:  
Birth Date:  
Height:  
Weight:  
Gender:  
Physician: Dr. Doctor   Patient ID:

Accession:  
Lab Accession:  
Date Collected:  
Received By Lab:  
Reported:

| Test Ordered (og/ml) | Lab Result | Assay Cutoff | Normalized Value | Expected Low | Range High | Range Interpretation | Medication Interpretation |
|---|---|---|---|---|---|---|---|
| Amphetamines FPIA Class | 2000 | 1000 | 4870.13 | | | | INCONSISTENT |
| Aumbetamines by CGMS | 900 | 125 | | | | | INCONSISTENT |
| Methamphetamine by GCMS | 1200 | 125 | | | | | INCONSISTENT |
| Barbiturates | POSITIVE | 300 | | | | | INCONSISTENT |
| Benzodiazepines FPIA Class | 265 | 100 | 645.29 | 634 | 1595 | NORMLO | |
| Alphabydroxyalprazolim by GCMS | 357 | 75 | | | | | Consistent |
| Alprazoliam by GCMS | 190 | 75 | | | | | Consistent |
| Noediazepam by GCMS | Negative | 75 | | | | | Consistent |
| Oxzepani by GCMS | Negative | 75 | | | | | Consistent |
| Diazepam By GCMS | Negative | 75 | | | | | Consistent |
| Lorazepam by GCMS | Negative | 75 | | | | | Consistent |
| Methadone FPLA Class | 1500 | 150 | 136 | 32 | 125 | NORMHI | |
| Propoxyphene FPIA Class | 2400 | 200 | 5844.16 | 3600 | 8400 | In Range | |
| Noepropoxyphene by GCMS | 2000 | 100 | | | | | Consistent |
| Propoxyphene by GCMS | 600 | 100 | | | | | Consistent |
| Opiates FPIA Class | 754 | 50 | 1144.96 | 205 | 530 | NORMHI | |
| Codeine by GCMS | Negative | 100 | | | | | |
| Morphine by GCMS | 105 | 100 | | | | | INCONSISTENT |
| Low levels of Morphine may be consistent with Poppy seed ingestion. | | | | | | | |
| Hydrocodome by GCMS | Negative | 100 | | | | | Consistent |
| Hydromorphone by GCMS | Negative | 100 | | | | | Consistent |
| Oxymorphone by GCMS | 500 | 100 | | | | | Consistent |
| Oxycodone by GCMS | 1200 | 100 | | | | | Consistent |
| Oxycodone by EIA | Positive | 100 | | | | | Consistent |
| Phencyclidine | Negative | 25 | | | | | |
| Suprenophine | Positive | 5 | | | | | Consistent |
| Codeine Screen Only | Positive | | | | | | |
| Barbinates | Positive | | | | | | INCONSISTENT |
| Butaldital by GCMS | POSITIVE | 50 | | | | | INCONSISTENT |
| Butaldital by GCMS | 597 | | | | | | |
| Phenobarbital by GCMS | Negative | 50 | | | | | Consistent |
| Secobarbital by GCMS | Negative | 50 | | | | | Consistent |
| Cocaine | Negative | 50 | | | | | Consistent |
| Benzoyleogomline by GCMS | Positive | | | | | | |
| Benzoyleogomline Consentration | POSITIVE 1821 | 10 | | | | | INCONSISTENT INCONSISTENT |

Supplemental explanation report 602

| Test | Explanation |
|---|---|
| Opiates FPIA Class<br>Oxymorphone by GCMS<br>Oxycodone by GCMS | The Oxycodone specific immunoassay is positive, which has been confirmed as Oxycodone and Oxymorphone by GC/MS. This is evidence of Oxycodone use within the past 2-3 days. |
| Carisoprodol<br>Carisoprodol by GCMS | Sample is negative for Meprobamate. This could be due to individual metabolism or to not taking the medication as prescribed. |
| Tramadol<br>Tramadol by GCMS | The GC/MS result confirms the presence of Tramadol. This is evidence of taking a Tramadol medication. |
| Gabapentin<br>Gabapentin by GCMS | The GC/MS result confirms the presence of Gabapentin. This is evidence of taking a Gabapentin medication. |

METHOD AND APPARATUS FOR GENERATING TOXICOLOGY REPORTS

CROSS-REFERENCE TO RELATED APPLICATIONS

The present application claims benefit to U.S. Patent Application No. 60/868,225, VIRTUAL TOXICOLOGIST SYSTEM, filed on Dec. 1, 2006, the entire contents of which are incorporated herein by reference.

BACKGROUND

Physicians use toxicology testing to determine the presence of chemical compounds in a patient's system. Often, a physician will send a toxicology sample to an outside testing lab to determine what is wrong with a patient. At the outside testing lab, the toxicology sample is put through a series of laboratory tests. The results of the tests are verified by a verification scientist. The verification scientist compiles the results and sends the results to the physician that requested the toxicology testing. In many cases, the results require interpretation. In those cases, the doctor typically calls the verification scientist. Calling the verification scientist may delay treatment of the patient. Additionally, the verification scientist may not be available when the physician calls, further delaying treatment.

In some cases, outside labs charge a fee for each call that a verification scientist receives from a physician. When the physician calls for an explanation of the test results, the extra fee is incurred. The extra fees add unnecessary expense to the treatment of a patient.

SUMMARY

The present disclosure provides methods and apparatuses for generating toxicology reports. Using the methods and apparatus disclosed herein, physicians can more easily understand toxicological lab test results. Physicians receive a toxicology report that explains, in plain language, the toxicological lab test results. A rules engine provides rules for interpreting the toxicological lab test results. Detailed explanations are associated with the rules, and the explanations appear on the toxicology report. The toxicology report greatly reduces the need for the physician to call the toxicology scientist.

Additional features and advantages are described herein, and will be apparent from, the following Detailed Description and the figures.

BRIEF DESCRIPTION OF THE FIGURES

FIG. 5 is an example test result page screenshot.

DETAILED DESCRIPTION

Figure 1:
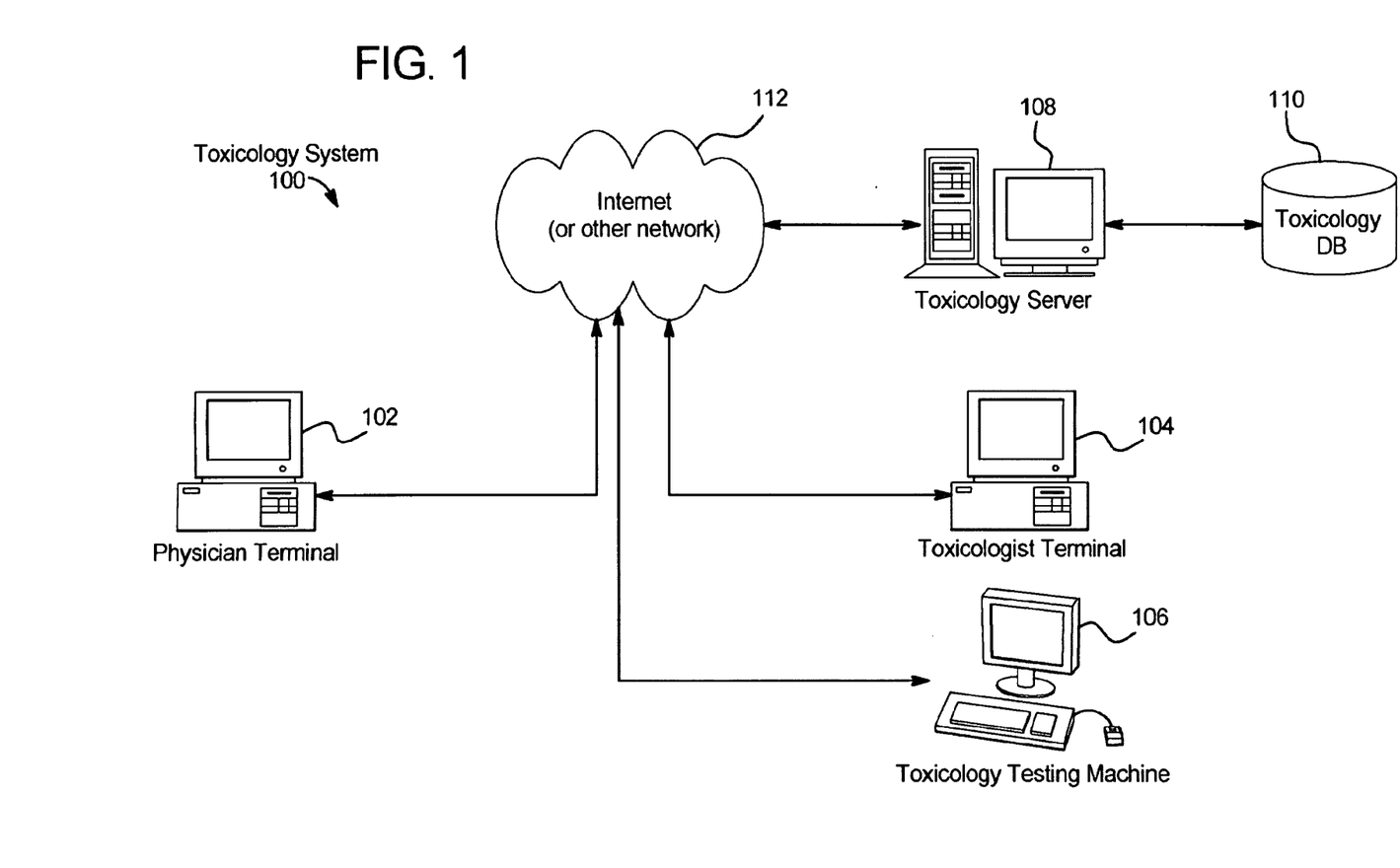
FIG. 1 is a high level block diagram of an example toxicology reporting system.

The present system is most readily realized in a network communications system. A high level block diagram of an exemplary network communications system 100 is illustrated in FIG. 1. The illustrated system 100 includes one or more physician terminals 102, one or more toxicologist terminals 104, one or more toxicology testing machines 106, one or more toxicology servers 108, and one or more toxicology databases 110. Each of these devices may communicate with each other via a connection to one or more communications channels 112 such as the Internet or some other data network, including, but not limited to, any suitable wide area network or local area network. It will be appreciated that any of the devices described herein may be directly connected to each other instead of over a network.

The toxicology server 108 stores a plurality of files, programs, and/or web pages in one or more toxicology databases 110 for use by the physician terminals 102, the toxicologist terminals 104, and/or the toxicology testing machines 106. The toxicology database 110 may be connected directly to the toxicology server 108 or via one or more network connections. The toxicology database 110 preferably stores toxicology test data, patient data, toxicology rules, etc. The patient data may include the patient's age, date of birth, height, weight, etc.

The toxicology testing machine 106 may be any device adapted to perform toxicological lab tests. The toxicology testing machine 106 may be connected to the toxicology terminal 104 and/or the toxicology server 108.

One toxicology server 108 may interact with a large number of terminals. Accordingly, each toxicology server 108 is typically a high end computer with a large storage capacity, one or more fast microprocessors, and one or more high speed network connections. Conversely, relative to a typical toxicology server 108, each physician terminal 102 or toxicologist terminal 104 typically includes less storage capacity, a single microprocessor, and a single network connection. A toxicology testing machine 106 may also have less storage capacity and a single microprocessor.

Figure 2:
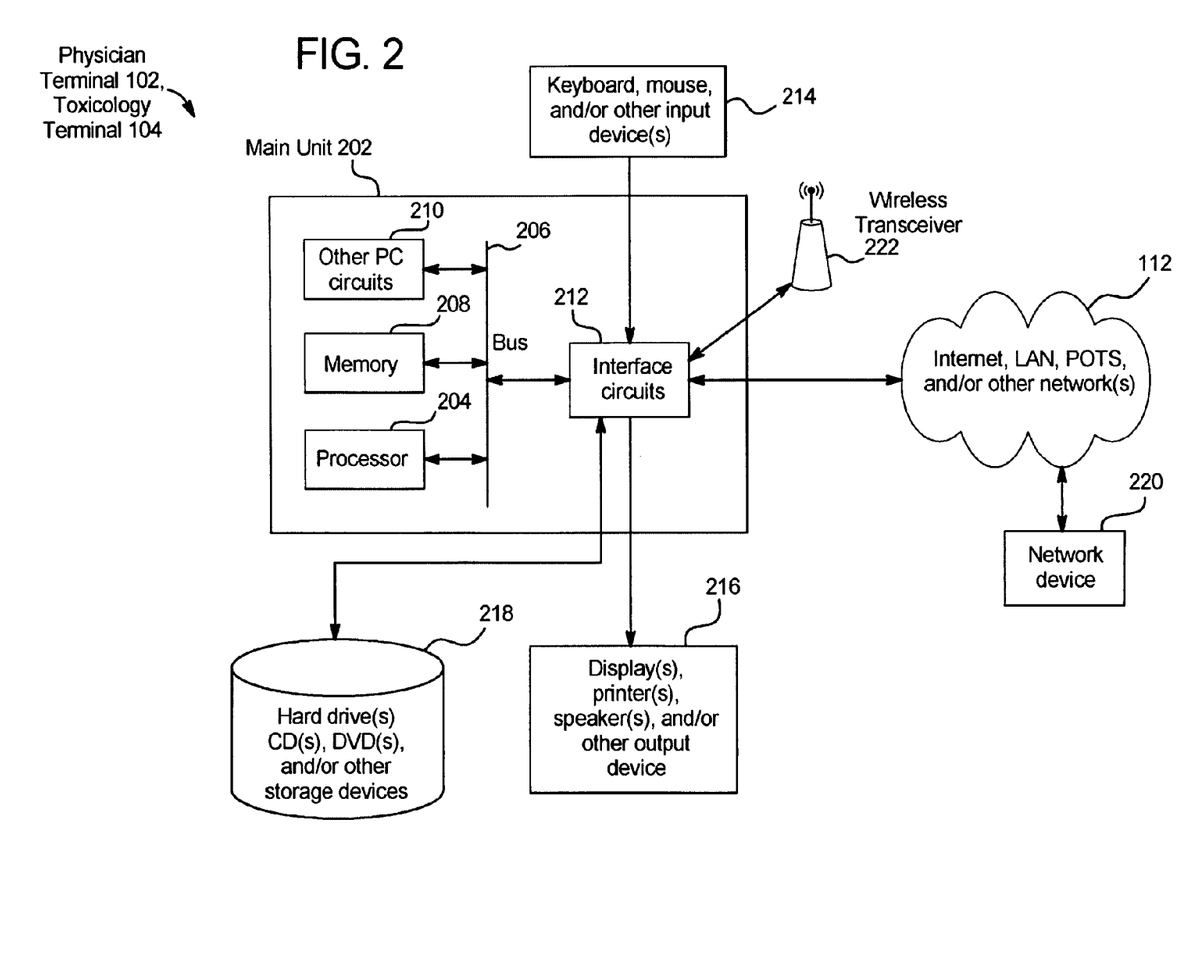
FIG. 2 is a more detailed block diagram showing one example of a client device.

A more detailed block diagram of a physician terminal 102 or toxicologist terminal 104 is illustrated in FIG. 2. The physician terminal 102 or toxicologist terminal 104 may include a personal computer (PC), a personal digital assistant (PDA), an Internet appliance, a cellular telephone, or any other suitable communication device. The physician terminal 102 or toxicologist terminal 104 preferably includes a main unit 202 which preferably includes one or more processors 204 electrically coupled by an address/data bus 206 to one or more memory devices 208, other computer circuitry 210, and one or more interface circuits 212. The processor 204 may be any suitable processor, such as a microprocessor from the INTEL PENTIUM® family of microprocessors. The memory 208 preferably includes volatile memory and non-volatile memory. Preferably, the memory 208 stores a software program that interacts with one or more of the other devices in the system 100 as described below. This program may be executed by the processor 204 in any suitable manner. The memory 208 may also store digital data indicative of documents, files, programs, web pages, etc. retrieved from one or more of the other devices in the system 100 and/or loaded via an input device 214.

The interface circuit 212 may be implemented using any suitable interface standard, such as an Ethernet interface and/or a Universal Serial Bus (USB) interface. One or more input devices 214 may be connected to the interface circuit 212 for entering data and commands into the main unit 202. For example, the input device 214 may be a keyboard, mouse, touch screen, track pad, track ball, isopoint, and/or a voice recognition system.

One or more displays, printers, speakers, and/or other output devices 216 may also be connected to the main unit 202 via the interface circuit 212. The display 216 may be a cathode ray tube (CRTs), liquid crystal displays (LCDs), or any other type of display. The display 216 generates visual displays of data generated during operation of the physician terminal 102, toxicologist terminal 104 or toxicology testing machine 106. For example, the display 216 may be used to display web pages received from the toxicology server 108. The visual displays may include prompts for human input, run time statistics, calculated values, data, etc.

One or more storage devices 218 may also be connected to the main unit 202 via the interface circuit 212. For example, a hard drive, CD drive, DVD drive, and/or other storage devices may be connected to the main unit 202. The storage devices 218 may store any type of data used by the physician terminal 102, toxicologist terminal 104 or toxicology testing machine 106.

The physician terminal 102, toxicologist terminal 104 or toxicology testing machine 106 may also exchange data with other network devices 220 via a connection to the network 112. The network connection may be any type of network connection, such as an Ethernet connection, digital subscriber line (DSL), telephone line, coaxial cable, etc. Users of a physician terminal 102, toxicologist terminal 104 or toxicology testing machine 106 may be required to register with the toxicology server 108. In such an instance, each user of a physician terminal 102, toxicologist terminal 104 or toxicology testing machine 106 may choose a user identifier (e.g., e-mail address) and a password which may be required for the activation of services. The user identifier and password may be passed across the network 112 using encryption built into the physician terminal 102, toxicologist terminal 104 or toxicology testing machine 106 browser. Alternatively, the user identifier and/or password may be assigned by the toxicology server 108.

Figure 3:
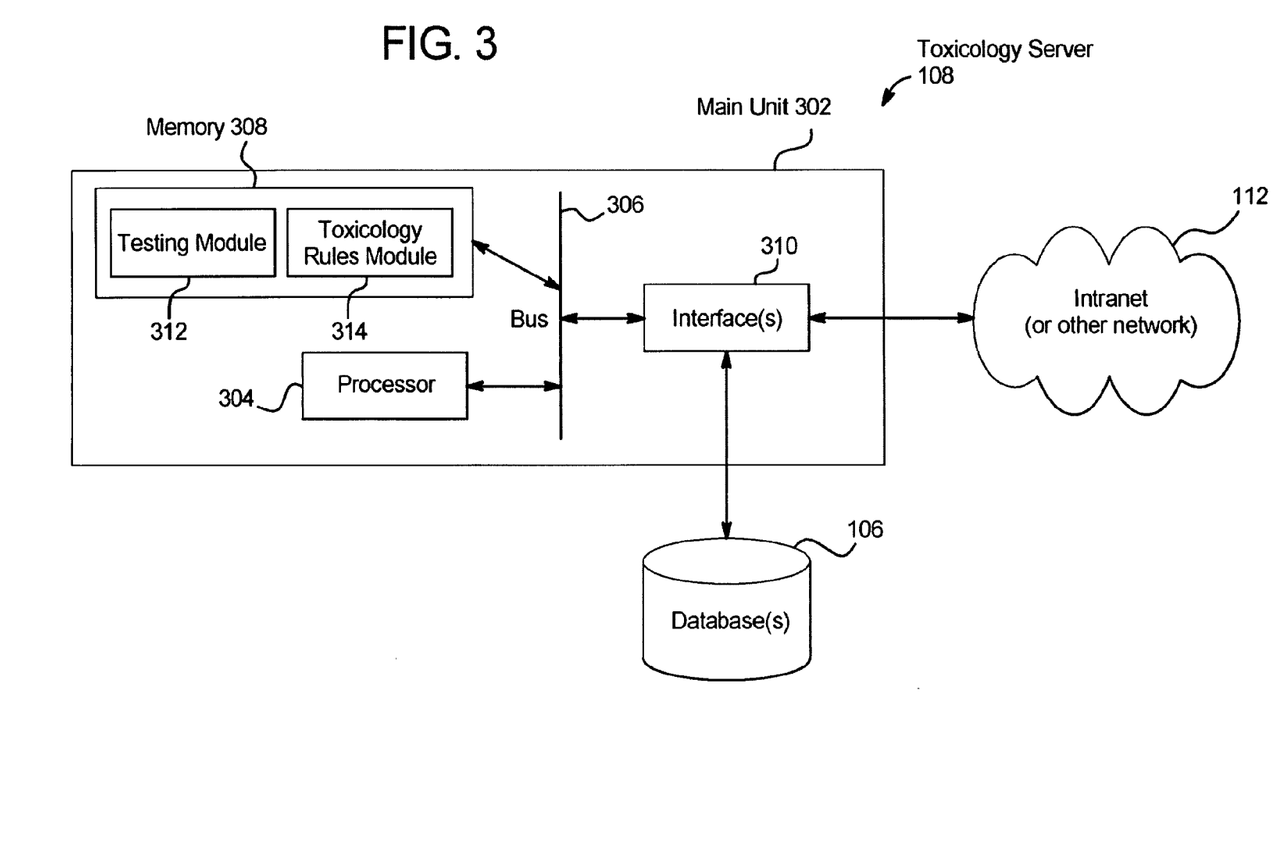
FIG. 3 is a more detailed block diagram showing one example of a server.

A more detailed block diagram of a toxicology server 108 is illustrated in FIG. 3. Like the physician terminal 102, toxicologist terminal 104 or toxicology testing machine 106, the main unit 302 in the toxicology server 108 preferably includes one or more processors 304 electrically coupled by an address/data bus 306 to a memory device 308 and a network interface circuit 310. The network interface circuit 310 may be implemented using any suitable data transceiver, such as an Ethernet transceiver. The processor 304 may be any type of suitable processor, and the memory device 308 preferably includes volatile memory and non-volatile memory. Preferably, the memory device 308 stores a software program that implements all or part of the method described below.

In particular, the memory preferably stores a testing module 312 and a toxicology rules module 314. The testing module 312 may transmit patient information from the toxicology database 110 to the toxicology testing machine 106. The testing module 312 may also determine which results are inconsistent with the patient medication history. For example, Codeine is a metabolite for Tylenol. If a patient is taking Tylenol and the test for codeine comes back negative, the testing module 312 may determine that the result is inconsistent. The testing module 312 may create a flag indicating the inconsistent result associated with the patient's test results.

The toxicology rules module 314 may use a rules engine to process the test results. For example, the rules engine may include a toxicology rule that a lower percentage of a metabolite in a toxicology sample than expected could be explained by a patient's higher metabolism. The toxicology rules module 314 may process the lab results using the rules engine and receive a rules engine output. The rules engine output may be in an electronic format, print out format, etc. The toxicology rules module 314 may use the rules engine output and an explanation chart to generate a supplemental explanation report. For example, using the rules engine output and an explanation chart, the toxicology rules module 314 may produce a supplemental explanation report stating, "Patient is prescribed Tylenol. Finding parent drug without metabolite could be due to individual metabolism."

These software modules 312, and 314 may be executed by the processor 304 in a conventional manner. However, some of the acts described in the method below may be performed manually or without the use of the toxicology server 108. The memory device 308 and/or a separate toxicology database 110 also store files, programs, web pages, etc. for use by other toxicology servers 108, physician terminals 102, toxicology terminals 104 and/or toxicology testing machines 106.

The toxicology server 108 may also receive subscription information from a physician at a physician terminal 102. The subscription information may include payment information. For example, the subscription information may include a credit card number, bank routing number, etc. The toxicology server 108 may store the subscription information in the toxicology database 110. The toxicology server 108 may assign a unique username and password to the physician at the physician terminal 102 after receiving the subscription information. The unique username and password may allow the physician to access the supplemental explanation report 600 page, which is described below.

The toxicology terminal 104 may be used to modify the toxicology rule. The toxicology terminal 104 may use a graphical user interface to modify a toxicology rule. For example, a toxicology rule may be represented in a graphical format and a toxicology scientist may use a graphical user interface to modify it. Additionally, the toxicology scientist using the toxicology terminal 104 may use a graphical user interface to add or delete a toxicology rule from the rules engine.

Figure 4:
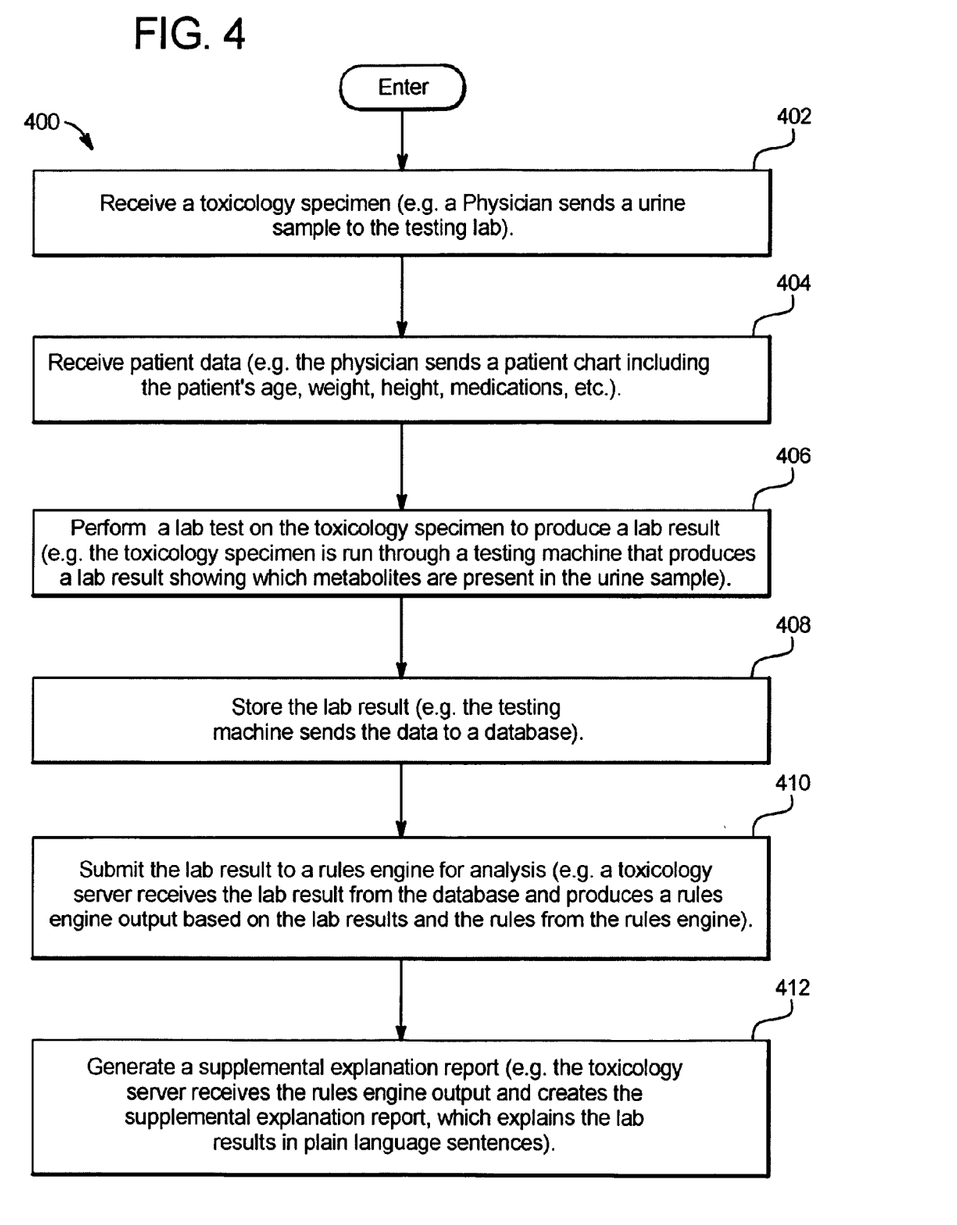
FIG. 4 is a flowchart of an example process for generating a toxicology report.

A flowchart of an example process 400 for generating toxicology reports is shown in FIG. 4. Preferably, the process 400 is embodied in one or more software programs stored in one or more memories and executed by one or more processors. Although the process 400 is described with reference to the flowchart illustrated in FIG. 4, it will be appreciated that many other methods of performing the acts associated with process 400 may be used. For example, the order of many of the acts may be changed, and some of the acts described may be optional.

In this example, the process 400 receives a toxicology sample (block 402). For example, a physician may send a toxicology sample to a testing lab. The toxicology sample may be a urine sample taken from a patient, a blood sample, etc. The toxicology lab may be a laboratory specializing in toxicology analysis. The toxicology lab may be associated with a hospital, a third party laboratory, associated with a research organization, etc.

The process 400 then receives patient data (block 404). For example, the physician may send a patient chart along with the specimen. The patient chart may contain the patient's age, sex, weight, height, medication information, etc. In another example, the physician may electronically transmit data indicative of the patient information from a physician terminal 102 to a toxicology server 108 at the testing lab.

The process 400 then performs a toxicological lab test on the toxicology sample to produce a lab result (block 406). For example, the toxicology sample may be analyzed using a toxicology testing machine 106. The toxicology testing machine 106 may perform a series of toxicology lab tests on the toxicology sample. For example, the toxicology testing machine 106 may chemically analyze the contents of the toxicology sample. The toxicology testing machine 106 may also produce a lab result. For example, the toxicology testing machine 106 may provide a print out. In another example, the toxicology testing machine 106 may transmit data indicative of a lab result to the toxicology server 108 or toxicology terminal 104.

The lab result may include data indicating the presence of metabolites in the toxicology sample. For example, the lab result may indicate the presence of methamphetamine. The lab result may also indicate the amount of the metabolite in the toxicology sample. For example, the lab result may indicate that the sample contains 1200 milligrams per milliliter (mg/ml) of methamphetamine.

Additionally, the lab result may include data indicating a drug-to-metabolite correlation. For example, the lab result may include data indicating whether an expected metabolite of a drug was found. For example, the drug may be Tylenol and the metabolite may be Codeine.

The lab result may be verified by a verification scientist. For example, a verification scientist may examine the lab result to ensure that the lab result is consistent with the patient information. The verification scientist may perform additional tests to ensure that the lab result is correct. The verification scientist may also run the toxicological lab tests again to ensure that the results are correct.

The verification scientist may also indicate that the lab results are verified. For example, the verification scientist may transmit data indicative of verification from the toxicology terminal 104 to the toxicology server 108. The toxicology server 108 may store the data indicative of the verification in the toxicology database 110 associated with the patient and/or lab results.

The process 400 then stores the lab result (block 408). For example, the toxicology server may store the lab result into a toxicology database 110. In another example, a toxicology scientist may enter the lab result into his or her toxicologist terminal 104 and transmit the data representing the lab result to the toxicology server 108. The toxicology server 108 may then store the lab result in a toxicology database 110.

The process 400 then submits the lab result to a rules engine for analysis (step 408). For example, the toxicology server 108 may transmit the lab result to a rules engine. The rules engine may reside in the memory of the toxicology server 108 itself or it may reside in the memory of another machine. The rules engine may include a toxicology rule stored in the toxicology database 110.

The toxicology rule may be a rule associated with a lab result and the patient medication information. For example, the toxicology rule may state that a patient taking Tylenol should test positive for Codeine.

The rules engine may produce a rules engine output. The rules engine output may be electronic data, a print out, etc. The rules engine output may include a code representing the result of the analysis by the rules engine. For example, the code may be an alphanumeric sequence of characters associated with a toxicology rule. The rules engine output may also include an explanation indicating the result of the analysis by the rules engine.

The process 400 then generates a supplemental explanation report. The toxicology server 108 may receive the rules engine output and produce a supplemental explanation report. For example, if the patient is not taking any medication and tests positive for Codeine and Tylenol, the toxicology server may use the rules engine output to generate a report stating "Tylenol and Codeine are indicative of use of a Tylenol medication. There is no prescription for Tylenol listed."

Figure 6:
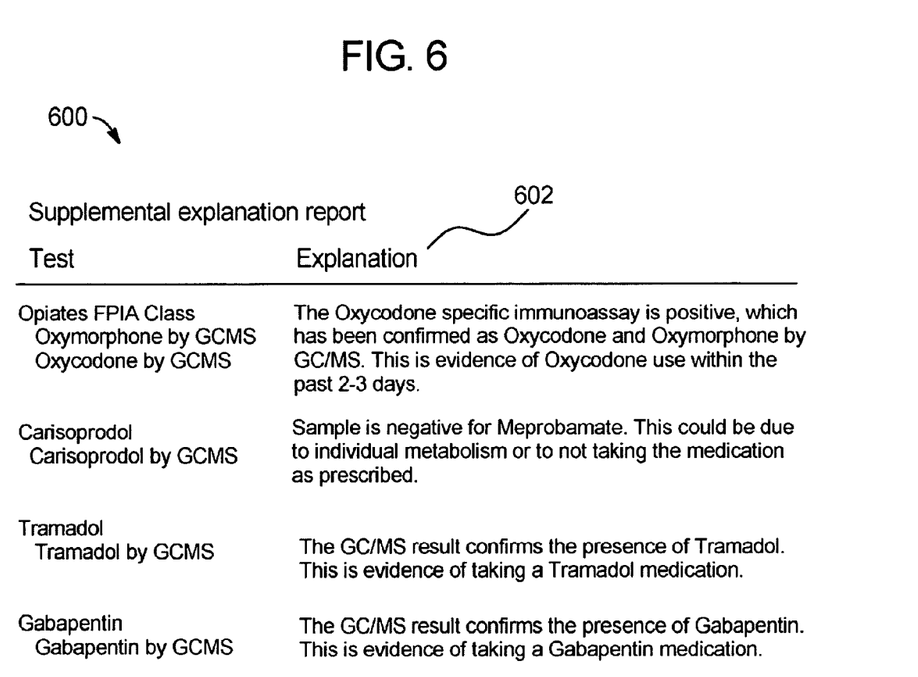
FIG. 6 is an example supplemental explanation report screenshot.

The supplemental explanation report may be in electronic format. For example, the toxicology server 108 may host a web page containing data indicative of the supplemental explanation report, an example supplemental explanation report page 600 is described below. The toxicology server 108 may require a physician, at a physician terminal 102, to log in with a unique username and password before accessing the supplemental explanation report. The supplemental explanation report may also be in a printed format. For example, the toxicology server 108 may create a print out, which includes the supplemental explanation report.

A screenshot of an example test result page 500 is presented in FIG. 5. Although the test result page 500 is described in reference FIG. 5, it will be appreciated that many other configurations are possible. For example, elements could be in different locations, elements could have different names, and elements could have different graphical representations.

For example, the test result page 500 may include patient information 502. The patient information 502 may include the patient name, birth date, height, weight, gender, unique identifier, etc.

The test result page 500 may also include a test result chart. The test result chart may contain a test result indicating the presence of a metabolite in the toxicology sample. The test result may also indicate the amount of metabolite in the toxicology sample. For example, the test result may state that 1200 mg/ml of methamphetamine are present in the toxicology sample. The test result may also indicate that the presence of methamphetamine is inconsistent with the patient's medication information.

A screenshot of an example supplemental explanation report page 600 is presented in FIG. 6. Although the test result page 600 is described in reference FIG. 6, it will be appreciated that many other configurations are possible. For example, elements could be in different locations, elements could have different names, and elements could have different graphical representations.

For example, the supplemental explanation report page 600 may contain an explanation chart 602. The explanation chart 602 may contain plain language explanations for a test result. For example, if a patient's medication information indicates that Meprobamate should be present in the toxicology sample but it is not, the explanation chart 602 may read, "Sample is negative for Meprobamate. This could be due to individual metabolism or to not taking the medication as prescribed." The supplemental explanation report may assist the physician in interpreting the lab result by providing a detailed explanation of the lab results.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for generating a toxicology report comprising:
   receiving a toxicology sample of a patient;
   receiving patient data about the patient, the patient data including patient medication information;
   performing a lab test on the toxicology sample to produce a lab result, the lab result including data indicative of the presence of a drug in the toxicology sample;

submitting the lab result to a rules engine to produce a rules engine output that describes a relationship between the lab result and the patient medication information, the rules engine including a toxicology rule that evaluates the data indicative of the presence of the drug and the patient medication information; and automatically generating a supplemental explanation report based on the lab result and the rules engine output, the supplemental explanation report including a plain language sentence that describes the relationship between the lab result and the patient medication information.

2. The method of claim 1, including verifying the lab results, wherein verification is performed by a verification scientist.

3. The method of claim 1, including modifying the toxicology rule using a graphical user interface.

4. The method of claim 1, including:
receiving a subscription for the supplemental explanation report from a physician; and
transmitting a document to the physician, the document containing the lab result and the supplemental explanation report.

5. The method of claim 1, wherein the patient data includes data indicative of the patient's age, height and weight.

6. The method of claim 1, wherein the lab test is for a drug-to-metabolite correlation.

7. The method of claim 1, wherein the supplemental explanation report includes an explanation for an inconsistent lab result.

8. The method of claim 1, wherein the plain language sentence describes at least one of: (i) whether the lab result is inconsistent with the patient medication information or (ii) a potential reason for an inconsistency between the lab result and the patient medication information.

9. The method of claim 8, wherein the patient medication information includes a prescription for the patient, and wherein the plain language sentence describes a relationship between the prescription and the lab result.

10. The method of claim, wherein the relationship between the lab result and the patient medication information includes an indication of whether the lab result and the patent medication information are inconsistent.

11. A system for generating a toxicology result, the system comprising:
a testing device to perform a lab test on a toxicology sample of a patient and to produce a lab result, the lab result including data indicative of the presence of a drug in the toxicology sample;
an input device to receive the lab result and patient data about the patient, the patient data including patient medication information;
a memory capable of storing the lab result and a toxicology rule that evaluates the data indicative of the presence of the drug and the patient medication information;
a processor to analyze the lab result based on the toxicology rule and to automatically create a supplemental explanation report, the supplemental explanation report including a plain language sentence that describes the relationship between the lab result and the patient medication information; and
an output device to display the supplemental explanation report.

12. The system of claim 11, wherein the input device receives data indicative of a verification of the lab result, wherein the data is entered by a verification scientist.

13. The system of claim 11, wherein the input device receives a modified toxicology rule in a graphical format.

14. The system of claim 11, wherein the input device receives subscription information from a physician, and wherein the output device displays the supplemental explanation report to the physician.

15. The system of claim 11, wherein the patient data includes data indicative of the patient's age, height and weight data.

16. The system of claim 11, wherein the lab test is for a drug-to-metabolite correlation.

17. The system of claim 11, wherein the supplemental explanation report includes an explanation for an inconsistent lab result.

18. The system of claim 11, wherein the plain language sentence describes at least one of: (i) whether the lab result is inconsistent with the patient medication information or (ii) a potential reason for an inconsistency between the lab result and the patient medication information.

19. The system of claim 18, wherein the patient medication information includes a prescription for the patient, and wherein the plain language sentence describes a relationship between the prescription and the lab result.

20. The system of claim 11, wherein the relationship between the lab result and the patient medication information includes an indication of whether the lab result and the patent medication information are inconsistent.

21. A computer readable medium storing instructions structured to cause a computing device to:
receive a lab result and patient data about a patient, the patient data including patient medication information and the lab result being based on a lab test preformed on a toxicology sample of the patient, wherein the lab result includes data indicative of the presence of a drug in the toxicology sample;
store the lab result and a toxicology rule that evaluates the data indicative of the presence of the drug and the patient medication information;
produce a rules engine output that describes a relationship between the lab result and the patient medication information by analyzing the lab result with a rules engine, the rules engine including the toxicology rule; and
automatically generate a supplemental explanation report based on the lab result and the rules engine output, the supplemental explanation report including a plain language sentence that describes the relationship between the lab result and the patient medication information.

22. The computer readable medium of claim 21, wherein the instructions are structured to cause the computing device to receive data indicative of a verification of the lab result, wherein the data is entered by a verification scientist.

23. The computer readable medium of claim 21, wherein the instructions are structured to cause the computing device to receive the toxicology rule in a graphical format.

24. The computer readable medium of claim 21, wherein the instructions are structured to cause the computing device to receive subscription information from a physician, and display the supplemental explanation report to the physician.

25. The computer readable medium of claim 21, wherein the patient data includes data indicative of the patient's age, height and weight data.

26. The computer readable medium of claim 21, wherein the lab test is for a drug-to-metabolite correlation.

27. The computer readable medium of claim 21, wherein the supplemental explanation report includes an explanation for an inconsistent lab result.

28. The computer readable medium of claim 21, wherein the plain language sentence describes at least one of: (i) whether the lab result is inconsistent with the patient medication information or (ii) a potential reason for an inconsistency between the lab result and the patient medication information.

29. The computer readable medium of claim 28, wherein the patient medication information includes a prescription for the patient, and wherein the plain language sentence describes a relationship between the prescription and the lab result.

30. The computer readable medium of claim 21, wherein the relationship between the lab result and the patient medication information includes an indication of whether the lab result and the patent medication information are inconsistent.

* * * * *

(12) EX PARTE REEXAMINATION CERTIFICATE (10805th)

United States Patent
Backer et al.

(10) Number: US 8,359,207 C1
(45) Certificate Issued: Feb. 2, 2016

(54) METHOD AND APPARATUS FOR GENERATING TOXICOLOGY REPORTS

(75) Inventors: Ronald C. Backer, Midland, TX (US); William Pace, Baytown, TX (US); Patricia Patrick, Decatur, GA (US); Sybil Patricia Lowry, Houston, TX (US); Shesh Rau, Naperville, IL (US); Joel McEndree, Midland, TX (US)

(73) Assignee: Ameritox, Ltd.

Reexamination Request:
No. 90/012,861, May 6, 2013

Reexamination Certificate for:
Patent No.: 8,359,207
Issued: Jan. 22, 2013
Appl. No.: 11/949,407
Filed: Dec. 3, 2007

Related U.S. Application Data

(60) Provisional application No. 60/868,225, filed on Dec. 1, 2006.

(51) Int. Cl.
*G06Q 50/00* (2012.01)

(52) U.S. Cl.
CPC ............................. *G06Q 50/00* (2013.01)

(58) Field of Classification Search
CPC ........................................ G06Q 50/00
USPC ................................................ 705/3
See application file for complete search history.

(56) References Cited

To view the complete listing of prior art documents cited during the proceeding for Reexamination Control Number 90/012,861, please refer to the USPTO's public Patent Application Information Retrieval (PAIR) system under the Display References tab.

*Primary Examiner* — Michelle Tarae (57) ABSTRACT

The present disclosure provides methods and apparatuses for generating toxicology reports. Using the methods and apparatus disclosed herein, physicians can more easily understand toxicological lab test results. Physicians receive a toxicology report that explains, in plain language, the toxicological lab test results. A rules engine provides rules for interpreting the toxicological lab test results, Detailed explanations are associated with the rules, and the explanations appear on the toxicology report. The toxicology report greatly reduces the need for the physician to call the toxicology scientist.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-30 are cancelled.

\* \* \* \* \*